United States Patent [19]
Wijay

[11] Patent Number: 6,053,940
[45] Date of Patent: Apr. 25, 2000

[54] VASCULAR STENT

[76] Inventor: Bandula Wijay, 1903 Carriage Creek Dr., Friendswood, Tex. 77546

[21] Appl. No.: 08/955,458

[22] Filed: Oct. 21, 1997

Related U.S. Application Data

[63] Continuation of application No. 08/546,277, Oct. 20, 1995.
[51] Int. Cl.⁷ .............................. A61F 2/06; A61F 2/02; A61M 29/02; A61M 29/00
[52] U.S. Cl. .................................. 623/1; 623/11; 623/12; 606/108; 606/191; 606/194; 606/195; 606/198
[58] Field of Search .................................. 623/1, 11, 12; 606/108, 191, 194, 195, 198

[56] References Cited

U.S. PATENT DOCUMENTS

| | | |
|---|---|---|
| Re. 34,037 | 8/1992 | Innue et al. . |
| 4,503,569 | 3/1985 | Dotter . |
| 4,580,568 | 4/1986 | Gianturco . |
| 4,732,152 | 3/1988 | Wallsten et al. . |
| 4,740,207 | 4/1988 | Kreamer . |
| 4,776,337 | 10/1988 | Palmaz . |
| 4,795,458 | 1/1989 | Regan . |
| 4,820,298 | 4/1989 | Leveen et al. . |
| 4,886,062 | 12/1989 | Wiktor . |
| 4,913,141 | 4/1990 | Hillstead . |
| 4,950,227 | 8/1990 | Savin et al. . |
| 4,964,853 | 10/1990 | Sugiyama et al. . |
| 4,969,458 | 11/1990 | Wiktor . |
| 4,990,151 | 2/1991 | Wallsten . |
| 5,100,429 | 3/1992 | Sinofsky et al. . |
| 5,108,416 | 4/1992 | Ryan et al. . |
| 5,133,732 | 7/1992 | Wiktor . |
| 5,135,536 | 8/1992 | Hillstead . |
| 5,139,480 | 8/1992 | Hickle et al. . |
| 5,158,548 | 10/1992 | Lau et al. . |
| 5,160,341 | 11/1992 | Brenneman et al. . |
| 5,163,951 | 11/1992 | Pinchuk et al. . |
| 5,163,952 | 11/1992 | Froix . |
| 5,163,958 | 11/1992 | Pinchuk . |
| 5,195,984 | 3/1993 | Schatz . |
| 5,197,978 | 3/1993 | Hess . |
| 5,213,561 | 5/1993 | Weinstein et al. . |
| 5,222,969 | 6/1993 | Gillis . |
| 5,222,971 | 6/1993 | Willard et al. . |
| 5,234,457 | 8/1993 | Anderson . |
| 5,258,042 | 11/1993 | Mehta . |
| 5,266,073 | 11/1993 | Wall . |
| 5,282,823 | 2/1994 | Schwartz et al. . |

(List continued on next page.)

FOREIGN PATENT DOCUMENTS

| | | |
|---|---|---|
| 90310775 | 10/1990 | European Pat. Off. . |
| 94302929 | 4/1994 | European Pat. Off. . |
| 94309839 | 12/1994 | European Pat. Off. . |

OTHER PUBLICATIONS

AngioStent Balloon Expandable Stent System, AngioDynamics Division of E–Z–EM, Inc., Sep., 1994 (brochure).
Gianturco–Roubin Flex–Stent Coronary Stents, Cook Cardiology, 1995 (brochure).
Medtronic WIKTOR GX, Medtronic Interventional Vascular, no date (brochure).
Miscellaneous literature regarding PS stent, no date.
Miscellaneous literature regarding Wiktor Stents, no date.
Miscellaneous literature regarding Wallstent, no date.

*Primary Examiner*—Mickey Yu
*Assistant Examiner*—Choon P. Koh
*Attorney, Agent, or Firm*—Duane, Morris & Heckscher LLP

[57] ABSTRACT

A flexible stent is provided that has features to minimize recoil and facilitate anchoring of the stent in a vascular passage. The design features sharp angulated bends. Other features include a rounded cross-section in the wire or stent components. Another feature is the bending of the angulated bends in a transverse plane to provide additional rigidity and an anchoring mechanism. Ties are provided in alignment or in staggered fashion, either semi-rigid or flexible, to allow the structure, which can be made of joined rings or a helical arrangement, to be more flexible to accommodate bends in the vascular system. The ties are also disclosed with a locking system involving bending the wire as it is formed into a helix in combination with crossties with loops which lock the stent in an expanded position.

32 Claims, 10 Drawing Sheets

U.S. PATENT DOCUMENTS

| | | |
|---|---|---|
| 5,282,824 | 2/1994 | Gianturco . |
| 5,287,861 | 2/1994 | Wilk . |
| 5,292,331 | 3/1994 | Boneau . |
| 5,304,121 | 4/1994 | Sahatjian . |
| 5,306,294 | 4/1994 | Winston et al. . |
| 5,314,472 | 5/1994 | Fontaine . |
| 5,334,201 | 8/1994 | Cowan . |
| 5,336,518 | 8/1994 | Narayanan et al. . |
| 5,342,348 | 8/1994 | Kaplan . |
| 5,344,426 | 9/1994 | Lau et al. . |
| 5,360,401 | 11/1994 | Turnland . |
| 5,368,566 | 11/1994 | Crocker . |
| 5,370,691 | 12/1994 | Samson . |
| 5,383,928 | 1/1995 | Scott et al. . |
| 5,389,106 | 2/1995 | Tower . |
| 5,391,172 | 2/1995 | Williams et al. . |
| 5,397,355 | 3/1995 | Marin et al. . |
| 5,403,341 | 4/1995 | Solar . |
| 5,421,955 | 6/1995 | Lau et al. . |
| 5,423,885 | 6/1995 | Williams . |
| 5,433,706 | 7/1995 | Abiuso . |
| 5,437,632 | 8/1995 | Engelson . |
| 5,439,444 | 8/1995 | Anderson et al. . |
| 5,439,445 | 8/1995 | Kontos . |
| 5,480,423 | 1/1996 | Ravenscroft et al. . |
| 5,496,365 | 3/1996 | Sgro .......... 623/1 |

VASCULAR STENT

This application is a continuation of copending application Ser. No. 08/546,277, filed on Oct. 20, 1995.

FIELD OF TIE INVENTION

The field of this invention relates to vascular stents that can be delivered to a predetermined position and allowed to spring outwardly or, in the alternative, which can be expanded in place.

BACKGROUND OF THE INVENTION

Vascular stents are structures that are designed to maintain the patency of a vessel in the body. The stent provides internal support to allow the circulation to proceed therethrough. Stents can be used in the vascular system in ureters, bile ducts, esophagus, and in many other tubular structures in the human body.

Stents can be tubular or can be made from wire. Stents are typically made from a metal or polymeric substance or a metal coated with polymers which are biocompatible or contain heparin to reduce blood clotting or other tissue reactions. Many prior designs have used a coil approach where a wire is helically wound on a mandrel. Yet other designs have evolved—braided wire mesh and angulated wire forms wrapped on a spindle to form a coil.

U.S. Pat. No. 5,292,331 by Boneau and U.S. Pat. No. 5,403,341 describe such wire forms. These devices have very poor radial support to withstand the hoop strengths of the artery or vein and further are not suitable for arteries that are bent or curved or for long lesions; multiple stent are required. These designs do not provide any support to hold the wall of the artery, other than the memory of the metal.

Wall Stent, produced by Pfizer Inc., is a braided wire tube. Although this stent is flexible so as to be placed in curved arteries or veins and other body cavities, it does not have any radial strength imparted to it by design.

Wiktor, U.S. Pat. Nos. 4,649,922; 4,886,062; 4,969,458; and 5,133,732 describe a wire form stent. He describes stents made of wire helix made of a preformed wire which is in the sinusoidal form, in which either all or some of the adjacent strands are connected.

Arthur Fontaine, U.S. Pat. No. 5,370,683, also describes a similar device where a flat wire form of sinusoidal shape is wound on a mandrel to form a helical coil. the wire bends are "U" shaped and are connected to alternate "U"-shaped bands.

Allen Tower, U.S. Pat. Nos. 5,217,483 and 5,389,106 describes a similar device where the wire is preformed to a sinusoidal shape and subsequently wound on a mandrel to form a helical coil.

All of the above-described art fails to provide radial support. The pre-shaped wire form (sinusoidal in most of the prior art) is wrapped on a mandrel to form a coil. However, the forces imported by the vessel wall's hoop strength are radially inward. In other words, the force is acting perpendicular to the plane of the U-shaped wire form. This means that the bends that are in the wire add no structural strength to the wire form to support the force produced by the wall, which is radially inward.

When we examine the simple coils, such as taught in Scott U.S. Pat. No. 5,383,928 or Gene Samson U.S. Pat. No. 5,370,691 or Rolando Gills U.S. Pat. No. 5,222,969, it is apparent that the spring coil will withstand substantial radial forces due to the vessel wall; however, all these stents are bulky in their pre-expanded form and are hard to place in small and curved arteries or veins of the body. Also, a major disadvantage of this design is that when the coil stent is placed in a curved artery or vein, it forms an "accordion" shape whereby some strands in the outer radius are spread and those of the inner radius are gathered. Spring coils can also "flip" to form a flat structure when a longitudinal force is applied on one side of the stent.

The other types of stents that have been developed are tube stents. Palmer, U.S. Pat. Nos. 4,733,665; 4,739,762; 7,776,337; and 4,793,348 describe such a tube stent of slotted metal tube. The slotted metal tube is expanded by a high-pressure balloon to implant the stent into the inside wall of the artery or vein.

Joseph Weinstein, U.S. Pat. No. 5,213,561 describes a similar stent made of tubular materials with slots cut into it. On expansion using a balloon, it forms a structure with diamond-shaped slots.

Henry Wall, U.S. Pat. No. 5,266,073 also describes a stent, tubular, that has slots machined into it. When expanded, the edges of the stent lock to form a cylinder. Not only is this device stiff and can only be used for short lesions, but also the diameter cannot be adjusted to meet the exact needs of the particular vessel but it is fixed to the predetermined sizes.

Lau and Hastigan, U.S. Pat. No. 5,344,426 describes a slotted tubular stent that has a structure similar to Henry Wall's but has provided prongs that will lock in as the stent is expanded.

Michael Marin, U.S. Pat. No. 5,397,355 also describes a tubular slotted stent with locking prongs.

All the above-described tube stents, although typically providing substantial radial support when expanded, are not flexible enough to be placed in curved vessels. Arteries and veins in the human body are mostly curved and are tapered. As such, these tube stents suffer from this main disadvantage.

European patent document 042172982 employs wires that are doubled up and whose ends are snipped off to make a given joint. Such doubling up at the junction of two elements with snipped off free ends creates a potential puncture problem upon radial expansion. The sheer bulk of the doubled up wires makes them rotate radially outwardly away from the longitudinal centerline of the stent while the plain ends on such an arrangement which are snipped off offer the potential of sharp points which can puncture or damage the intima On the other hand, the apparatus of the present invention, employing sharp angles, as defined, avoids this problem in an embodiment which illustrates a continuous wire or wire-like member bent into a sharp angle. This type of structure alleviates the concerns of sharp edges, as well as the tendency of a doubled up heavy joint to rotate outwardly toward the intima upon radial expansion of the stem, as would be expected in the EPO reference 042172982.

Often these stents are layered with polymeric sheaths that are impregnated with biocompatible substances or can be coated with heparin or hydrogel Most sheath-type coatings reduce endothelial cell growth through the stent, which is a major requirement in successful stenting of body cavities such as arteries and veins.

Several parameters in design of stents are important. Of the more important parameters is the issue of recoil. Recoil deals with the memory of the stent material which, generally speaking, upon expansion in the blood vessel will want to recoil back to its original shape. This can be problematic because it is desirable for the stent, once expanded, to remain in good contact with the vessel wall to avoid longitudinal shifting. Furthermore, any recoil constricts the flow passage and presents a greater portion of the stent in the blood flowpath, thus creating additional complications due to the turbulence which ensues.

Related to the concern regarding recoil is another concern regarding component twist. This phenomenon generally occurs when the cross-sectional area of the components is rectangular, such as when the stent is manufactured from a cylindrical piece which is then cut by lasers or other means to form the particular pattern. Particularly in the honeycombed designs involving the use of square or rectangular element cross-sections, radial expansion of such stents generally results in a twist of the component segments such that they extend into the flowpath in the artery or vein. Again, this causes turbulence which is undesirable.

Related to the problem of recoil or constriction after expansion is the ability of the stent to anchor itself in the vascular wall. An anchoring system that does not cause trauma is a desirable feature not found in the prior art.

Yet other considerations which are desirable in a stent not found in the prior art is the flexibility to be maneuvered around bends in the vascular system, coupled with the ability to conform to a bend without kinking or leaving large open areas. The stents of the present invention have the objective of addressing the issue of recoil, as well as providing an anchoring mechanism to fixate the stent once set Several of the designs incorporate flexibility to allow the stent to follow a bend or curve in a vascular flowpath while at the same time providing sufficient radial deformation to ensure proper fixation while minimizing angular twisting movements of the stent components to minimize turbulence through the stent

SUMMARY OF THE INVENTION

A flexible stent is provided that has features to minimize recoil and facilitate anchoring of the stent in a vascular passage. The design features sharp angulated bends. Other features include a rounded cross-section in the wire or stent components. Another feature is the bending of the angulated bends in a transverse plane to provide additional rigidity and an anchoring mechanism. Ties are provided in alignment or in staggered fashion, either semi-rigid or flexible, to allow the structure, which can be made of joined rings or a helical arrangement, to be more flexible to accommodate bends in the vascular system. The ties are also disclosed with a locking system involving bending the wire which is formed into a helix in combination with crossties with loops which lock in the bends to lock the stent in an expanded position.

DETAILED DESCRIPTION OF THE PREFERRED EMBODIMENT

Figure 1:
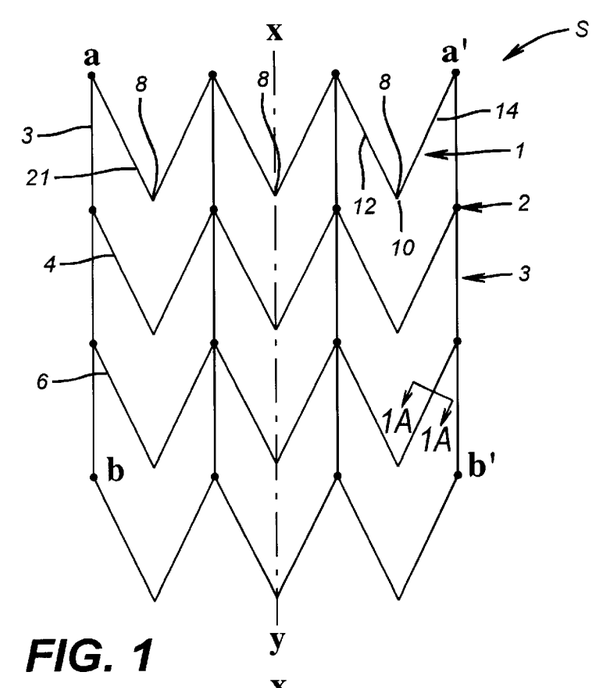
FIG. 1 is a flattened view of a stent, which would normally be formed by joining points a to a' and b to b', illustrating the sharp, angulated aspects of the stent where a series of parallel rings are used with crossties.
Figure 2:
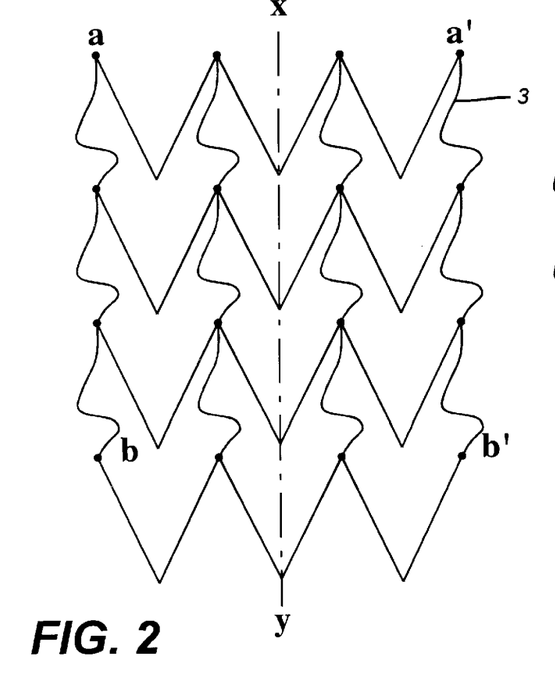
FIG. 2 is similar to the view of FIG. 1, except the crossties have additional flexibility.
Figure 2A:
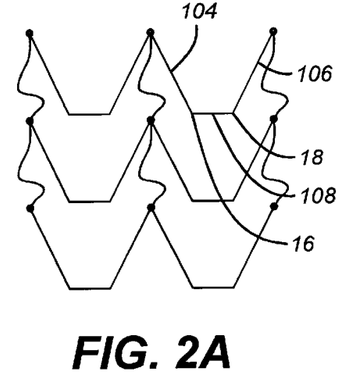
FIG. 2A is an alternative embodiment to FIG. 1.
Figure 19:
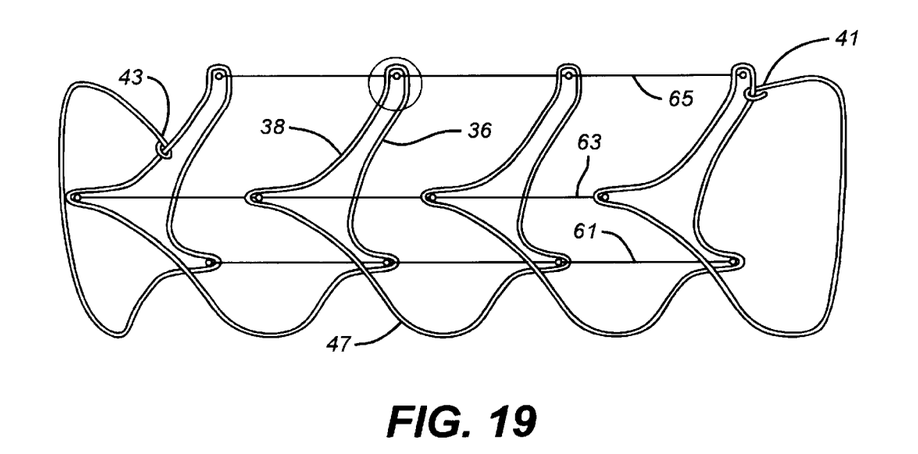
FIG. 19 illustrates a spirally wound stent employing sharp angulated bends with a transverse bend located adjacent the angulated bend and shown in a closeup inside the circle.
Figure 19A:
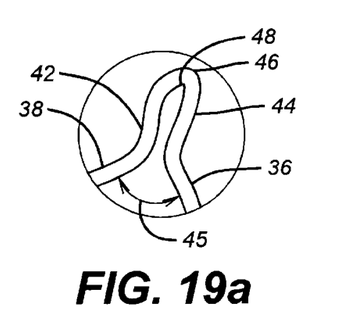

FIG. 1 illustrates, in flattened form, one of the embodiments of the stent of the present invention. In order to form the stent, the points labeled "a" and "a'" are, in fact, joined together, as are the points "b" and "b'," to form a tubular shape for the stent. The stent is shown in flattened form to illustrate its components. The stent can be cut from a tubular member by known techniques, such as lasers, or can be assembled from wire material. Wire or wire-like material is intended to refer to the components of a stent, regardless of the manufacturing technique that is used. As illustrated in FIG. 1, wire 1 is bent in a predetermined shape and is disposed parallel to wire 4, which is in turn parallel to wire 6. When formed into the shape of a stent by connecting points a and a' and b and b', wire 1 is a ring made of a plurality of sharp bends 8. FIG. 1 shows similar bends in wire 4 and 6. In this embodiment, the bends are sharp as opposed to being rounded. The embodiment in FIG. 1 shows a general V-shape involving an apex at 10, formed by two segments 12 and 14, typically. Segments 12 and 14 can approach each other at a "sharp angle" but at a point short of the apex. They can be bent again into a near-parallel relation with a rounded apex. In this configuration, as shown in FIG. 19, there is still a "sharp angle" 40, even if the apex has a rounded feature to it. A sharp angle indicates an approach of two segments to each other to meet at a point or to come very close to each other where, although differently joined, they effectively, for resistance to hoop stress purposes, still function similarly as though the segments met at a point. FIG. 2A shows the use of U-shapes with sharp bends at apexes 16 and 18, typically.

Figure 1A:
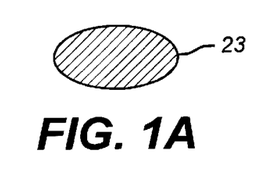
FIG. 1A is a view taken along lines A—A of FIG. 1, showing the oval cross-section of the wire-like material component.

Referring again to FIG. 1, wire 1 is secured to wire 4 by crossties such as 3, which can be of a wire material having similar or somewhat different characteristics than wires 1, 4, or 6. In the embodiment shown in FIG. 1, the crossties 3 are relatively straight and in the same position as between wires 1 and 4 compared to wire 4 with wire 6. In all the embodiments, crossties such as 3 can span adjacent windings or rings or can span over several, all without departing from the spirit of the invention. These crossties 3 may be staggered such as, for example, shown in FIG. 9. FIG. 1A shows the cross-section of the wire which in one embodiment is an oval, although the preferred embodiment is rounded.

Usage of rings (see FIG. 1) or a continuous member (see FIG. 19) turned in a helical manner are each considered to be structures that employ "windings."

The stent depicted in FIG. 1 can be assembled from wire components or can be cut from a solid tube using known laser cutting techniques. FIG. 2 is similar to FIG. 1 except that the crossties 3 are made with a certain amount of flexibility generally put into them by a plurality of bends, although other means for providing flexibility in the crossties 3 are within the purview of the invention. Again, in the view of FIG. 2, the stent is flattened out into one plane. The flexible crossties allow greater accommodation of the stent shown in FIG. 2 when advanced into a vascular cavity that contains bends in one or more planes. To accommodate a bend, some of the crossties 3 on the inside of the bend are placed in compression and can easily compress, due to the flexibility revealed in the design of FIG. 2, while on the opposite side of the bend, the crossties 3 are in tension and elongate to accommodate the total stent structure in being positioned in a turn that exists in one or more planes. As previously stated, U-shapes may be used as long as the turns or apexes 16 and 18 are "sharp" corners rather than a bending of the wire around a relatively long radius. The rationale is that the sharp corners, whether in a U-shape or a V-shape, as shown in FIG. 1, when plastically deformed such as when placing the stent in position, do not recoil but instead hold their plastically deformed position much better, and therefore maintain their fixation to the vessel wall. In combination with the crossties in FIGS. 1 or 2 that have some flexibility, bends of various degrees of sharpness can be traversed by the stent without kinking. The design in FIG. 2A can have the second bend feature, as illustrated in FIG. 19, where segments 104 and 106 are bent, raising the apexes 16 and 18 into another plane. Similarly, the apex detail shown in FIG. 19 can be used as the apex illustrated as 16 and 18 in FIG. 2A. The included angles in FIG. 2A may be acute, right, or obtuse angles. Other shapes with "sharp" angles can be used such as [ or Z shapes, for example, without departing from the spirit of the invention.

Figure 3:
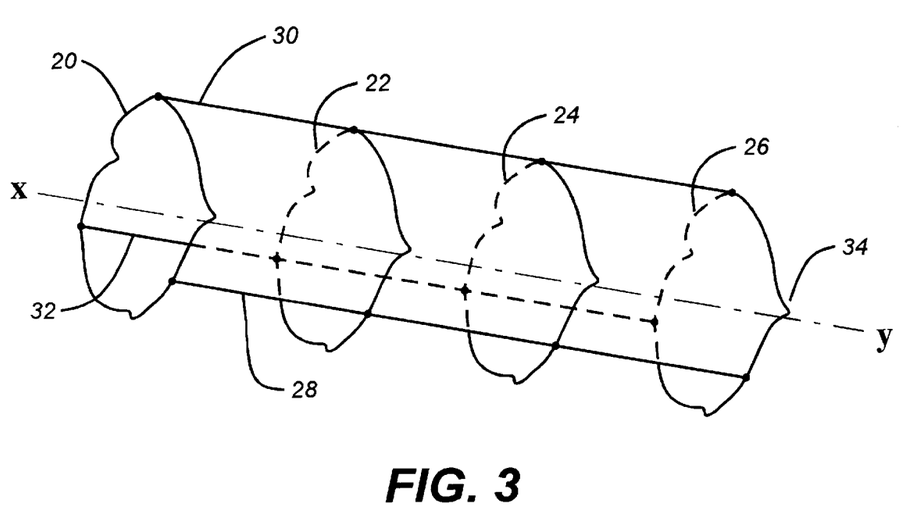
FIG. 3 is a perspective view of the stent in FIG. 1, showing the additional feature of bending the angulated wire segments in a transverse plane.

FIG. 3 illustrates the use of bent wires or wire-like elements formed into rings such as, for example, 20, 22, 24, and 26. Longitudinally aligned crossties 28, 30, and 32 hold the rings to each other to create the stent structure, which is shown in perspective with its center axis labeled "x–y." Each of the rings 20–26, besides having the sharp bend illustrated in FIG. 1 or 2A, also has a second bend such as, for example, 34. The second bend 34 is in a plane traversing the plane of the bends illustrated, for example, in FIG. 1 for wire 1. FIG. 19 more readily illustrates this principle. In that figure, the sharp bends are formed, for example, in a particular segment of the stent by wire segments 36 and 38. It should be noted that the embodiment of FIG. 19 is a continuously wound helix with ends 40 and 42 looped back around and connected at either end of the stent, as shown in the figure. This is to be distinguished from the design shown in FIG. 3 where a series of rings of wire 20–26 are employed.

Looking now at the segments 36 and 38 in the exploded portion of FIG. 19, it is seen that a sharp angle between them, represented by arrow 40, is formed. However, rather than connecting at an acute angle, such as shown in FIG. 1, or obtuse angles or acute angles as could be shown in FIG. 2A, segments 36 and 38 have parallel or near-parallel components 42 and 44, which are bent in a different plane than the main portion of segments 36 and 38. Eventually, the segments 42 and 44 come together at an apex 46, which in the preferred embodiment should have a small turning radius 48.

Figure 6:
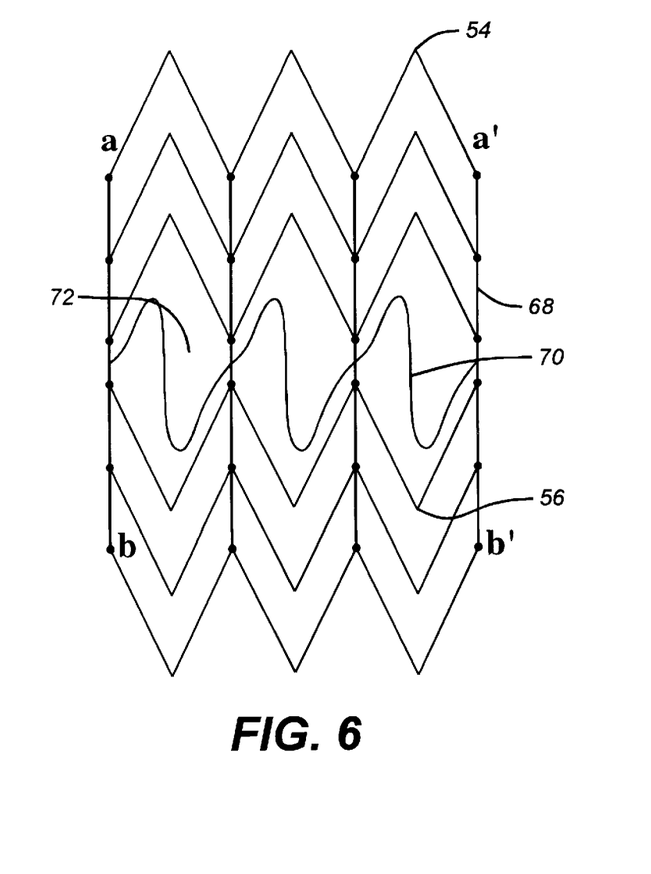
FIG. 6 is yet another embodiment showing the angulated wire components with a combination of different crossties, some having more flexibility than others.
Figure 13:
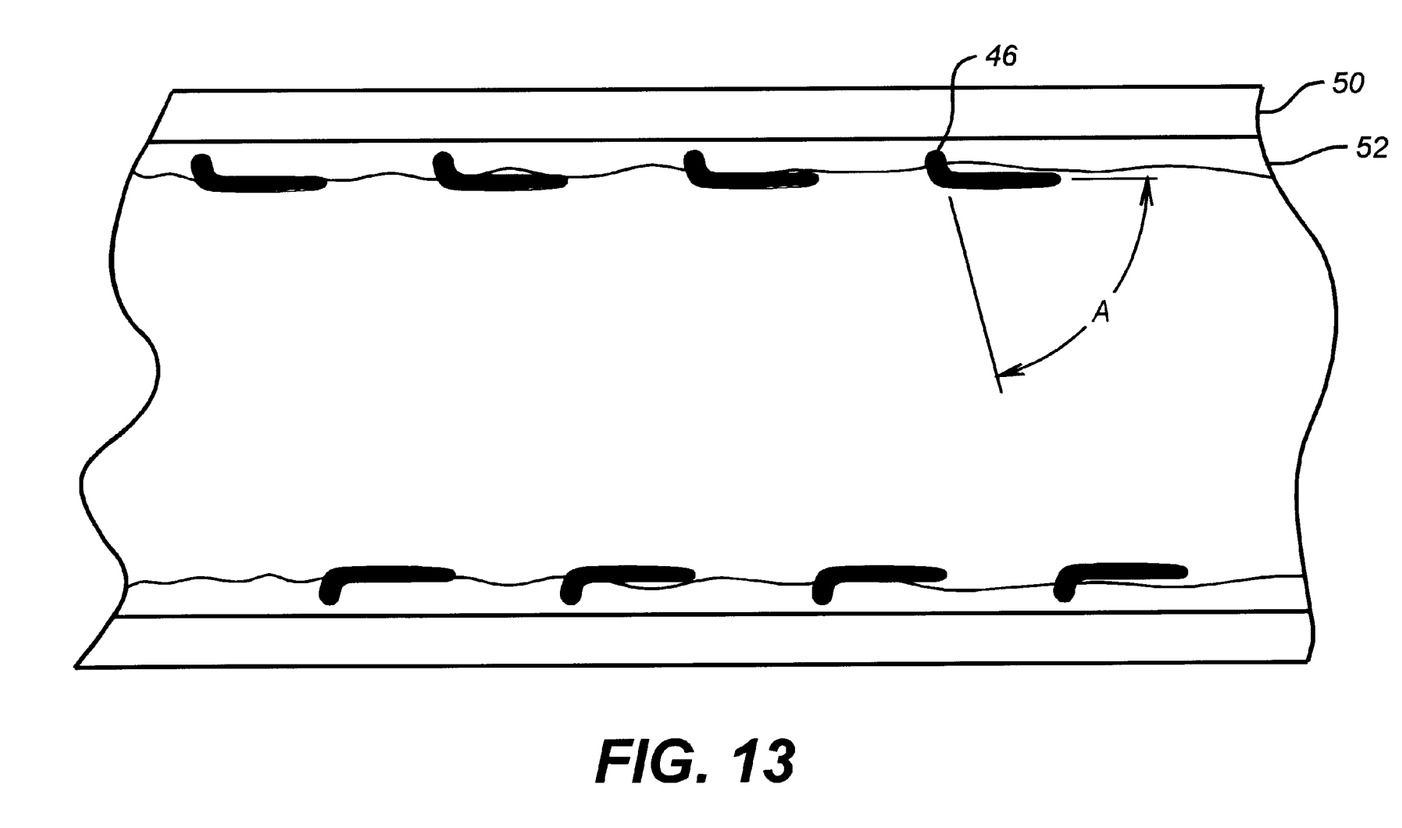
FIG. 13 is a sectional elevational view illustrating how the anchoring mechanism of the bend in the transverse plane operates.

As seen in FIG. 13, the apex 46 is outwardly oriented toward the vessel wall 50. Typically, the vessel has an internal build-up 52. The expanded stent, as shown in FIG. 13, uses the parallel components 42 and 44, forming the apex 46, as an anchoring mechanism. While all the anchors in FIG. 13 are illustrated to be in the same orientation, some of the anchors can be in reverse orientations to other anchors, thus putting them in nonparallel planes, thereby stabilizing the stent against longitudinal movement in either direction. Such can be the case when using a design such as illustrated in FIG. 6, where a V-shaped acute angle design is illustrated. Taking the design of FIG. 6 and employing the feature of turning up the apex 54, it can readily be seen that if apex 56 is also turned outwardly, then an anchoring system would be employed where some of the extending segments, as shown in FIG. 19, would be oriented in the direction shown in FIG. 13, while others would have the opposite orientation.

Figure 4:
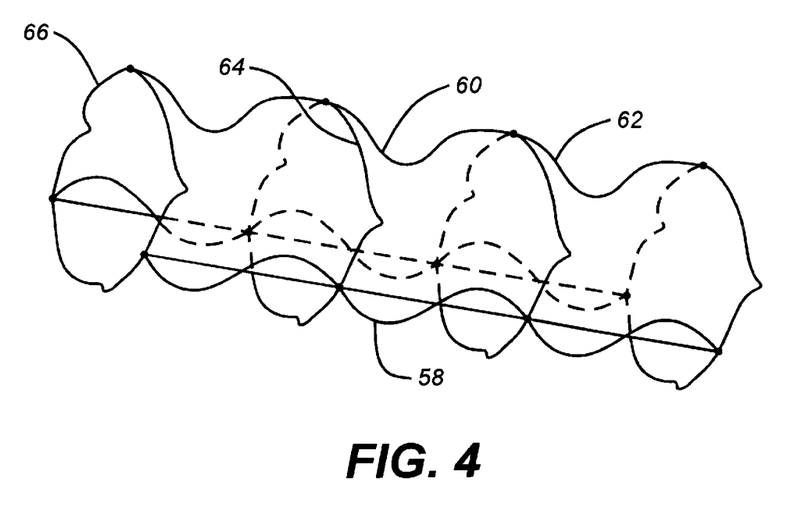
FIG. 4 is an alternative to the embodiment in FIG. 3, shown in a perspective view, illustrating the use of crossties with additional flexibility.

The embodiment shown in FIG. 4 is similar to the embodiment of FIG. 3 except that the crossties 58 have additional flexibility in them. Thus, for example, if the stent of FIG. 4 were placed into a turn in a vascular structure, where the inside of the turn is represented by crossties 60, those crossties would tend to compress while the outside of the turn, represented by crossties 58 and 62, would tend to lengthen. This structure should be compared to a simple helical spring which, although will exhibit a tendency to have its coils come closer together on the inside of a turn and further apart on the outside, will exhibit the disadvantageous attributes of creating unduly large openings on the outside of the turn where the coils move away from each other. In the design of the present invention as, for example, shown in FIG. 4, while the rings such as 64 and 66 may move away from each other, adjacent crossties 62 and 58 will continue to bridge the gap between the rings to prevent unduly large openings in the stent which could promote significant tissue growth therethrough.

Figure 5:
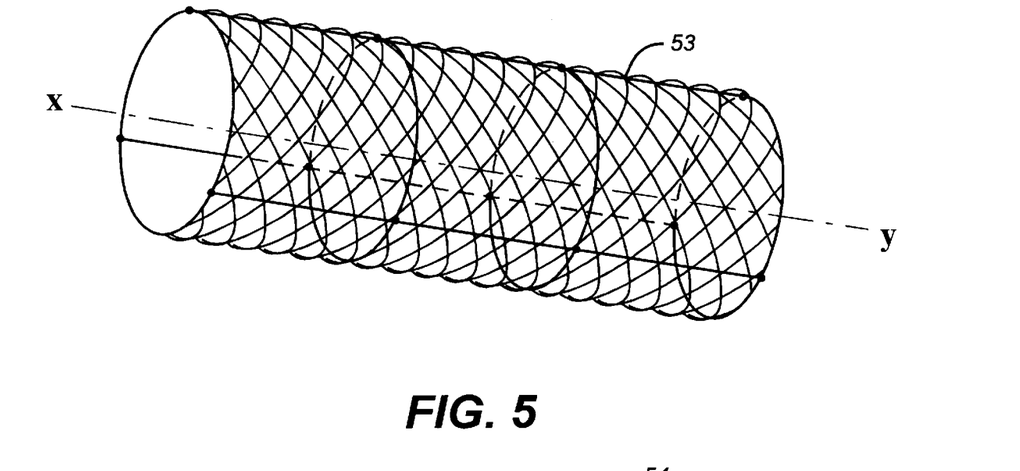
FIG. 5 is another perspective view, showing the exterior coating in the form of a mesh on the outer periphery of the stent.

FIG. 5 illustrates the embodiment of FIG. 3, with an external covering on the stent which can be made of a biocompatible material or, in the alternative, can be coated with heparin or hydrogel. These sheath-type coatings prevent endothelial cell growth over the stent, which is a significant requirement in successful stenting of body cavities such as veins and arteries.

The embodiment shown in FIG. 6 is again a wire ring design with crossties similar to that shown in FIG. 1, except some of the wire rings have reverse orientation of their apexes, such as 54, to other rings which have their apexes pointing in the opposite direction, such as 56. While the design in FIG. 6 employs crossties such as 68, other flexible wire members 70 are placed in the transition zone 72 to fill in any large gaps in the transition zone 72. With the design of FIG. 6, the most likely flexing of the stent around a turn in a vascular flowpath will be adjacent to the transition zone 72. The wire members 70 have a plurality of bends to give them the flexibility, not only longitudinally but radially, when placing the stent of FIG. 6.

Figure 7:
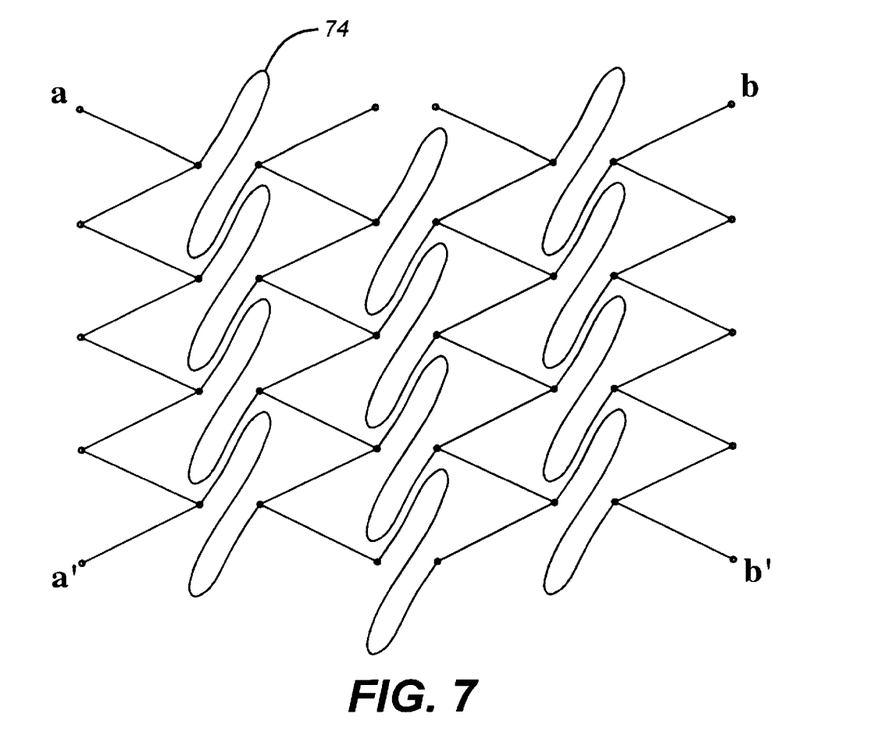
FIG. 7 is yet another embodiment illustrating the angulated wire members being out of phase as between one row and another and connected in that embodiment by crossties with flexibility.

FIG. 7 illustrates the "sharp" angle design involving a generally V-shaped wire ring connected to its adjacent ring by crossties 74. Crossties 74 have a plurality of bends, as illustrated in FIG. 7, to provide longitudinal flexibility of the stent to bend around a turn in the vascular path.

Figure 8:
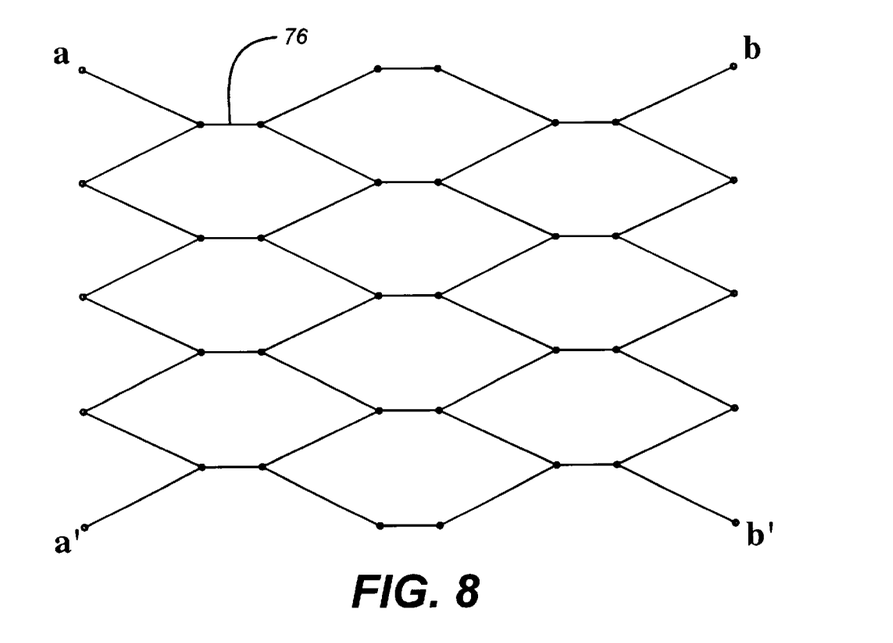
FIG. 8 is the embodiment of FIG. 7, using crossties with less flexibility.

FIG. 8 is similar to FIG. 7 except that the crossties 76 are straight rather than having a plurality of bends. The design of FIG. 8 has somewhat less flexibility with regard to being manipulatable around sharp bends but still retains additional longitudinal flexibility than prior designs.

Figure 9:
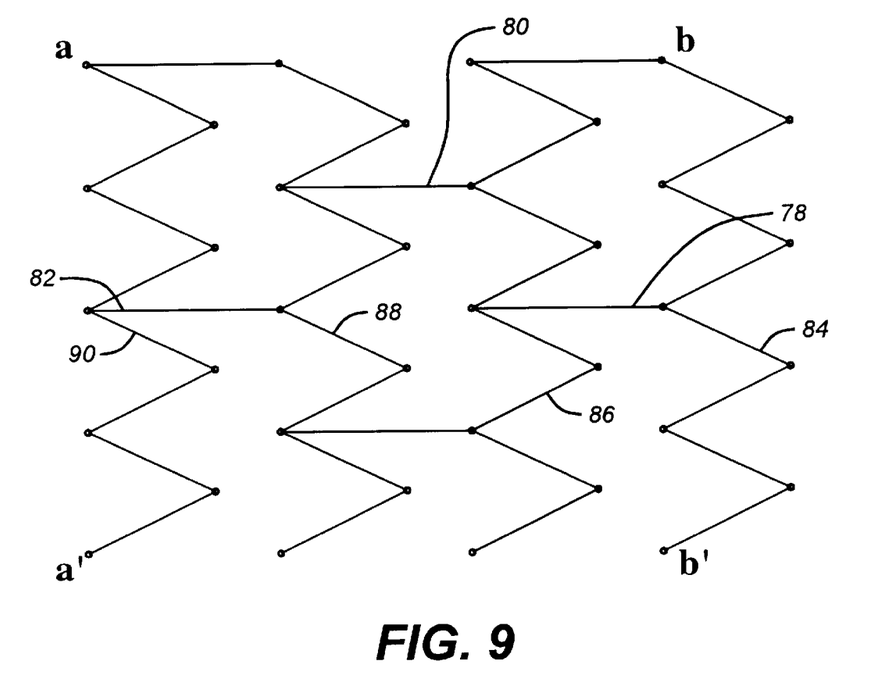
FIG. 9 illustrates the angulated wire components making up the stent being in alignment from one row to the next, with crossties offset circumferentially.

FIG. 9 illustrates the staggering circumferentially of the crossties 78 and 80. As seen in FIG. 9, looked at in a longitudinal line along the axis of the stent, crosstie 70 is aligned with crosstie 82, but the ties skip a row of wires. Accordingly, crosstie 78 holds together in one location wire 84 to wire 86. In that same longitudinal line, there is a gap with no crosstie between wire ring 86 and wire ring 88. Crosstie 82 is then in the same longitudinal line holding together wire rings 88 and 90. Where there is no connection between wire rings 86 and 88, aligned with crossties 78 and 82, the next crosstie appears either above or below, such as that denoted by 80, which is circumferentially offset.

Figure 10:
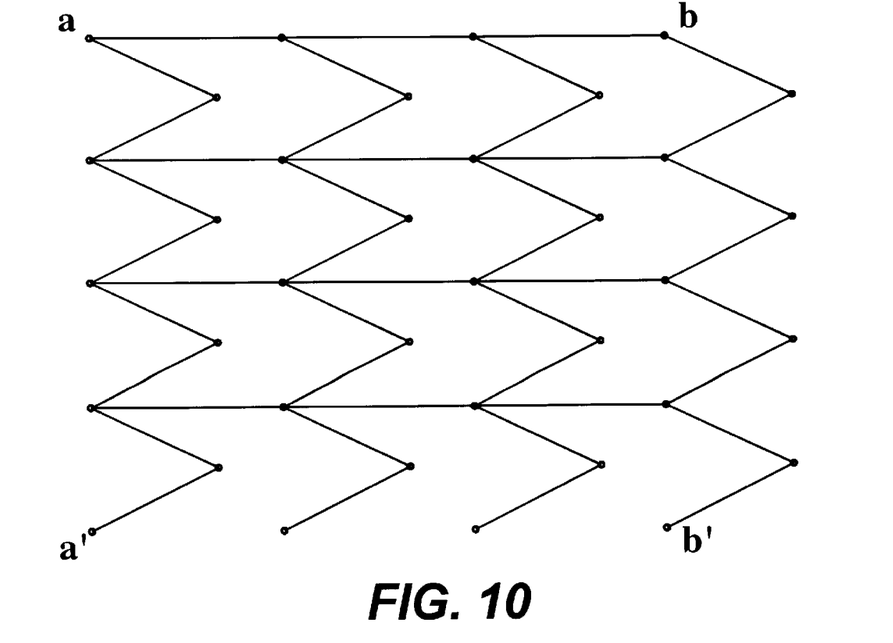
FIG. 10 is the view of FIG. 9, with the crossties in alignment longitudinally and circumferentially.

FIG. 10 is similar to FIG. 9 except that the crossties are in longitudinal alignment instead of being offset circumferentially. It is clear that the design of FIG. 9 is more longitudinally flexible with respect to being workable around bends in the vascular cavities, while both designs of FIGS. 9 and 10 can flex because of their construction without twisting of the individual segments of each wire ring.

Figure 11:
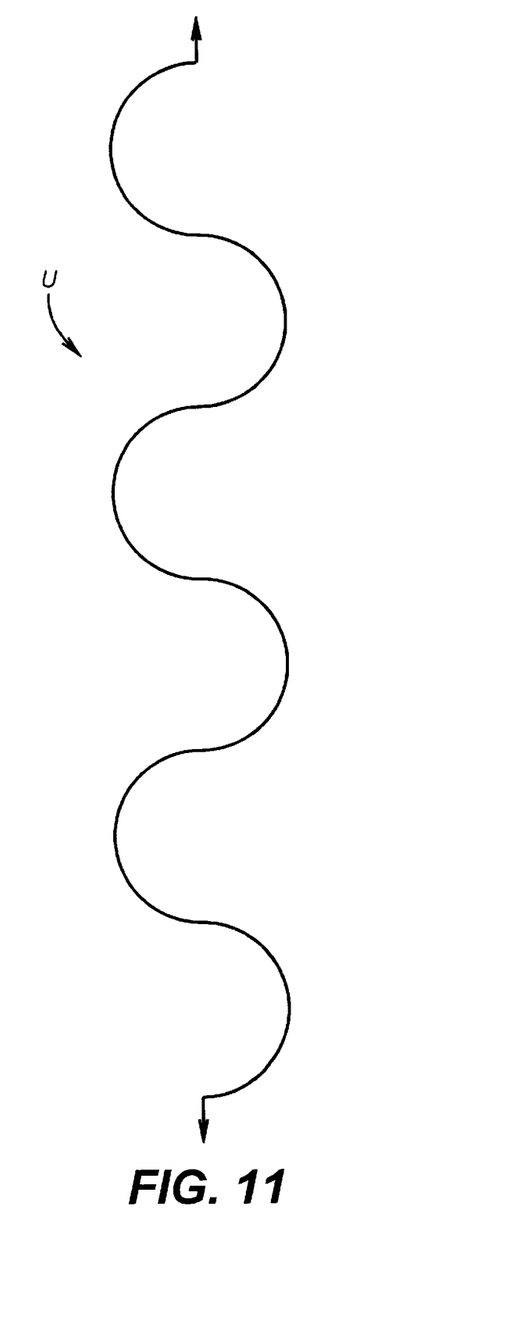
FIG. 11 is a close-up view of a wire prior to its being coiled into a helix as shown in FIG. 14.
Figure 12:
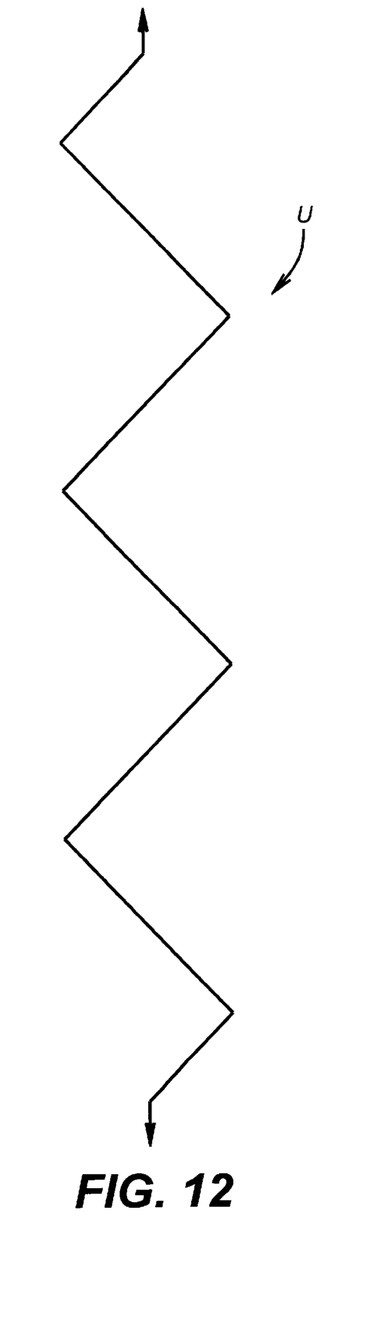
FIG. 12 is an alternative embodiment to the forming of the wire in FIG. 11 as it relates to the embodiment of FIG. 14.
Figure 14:
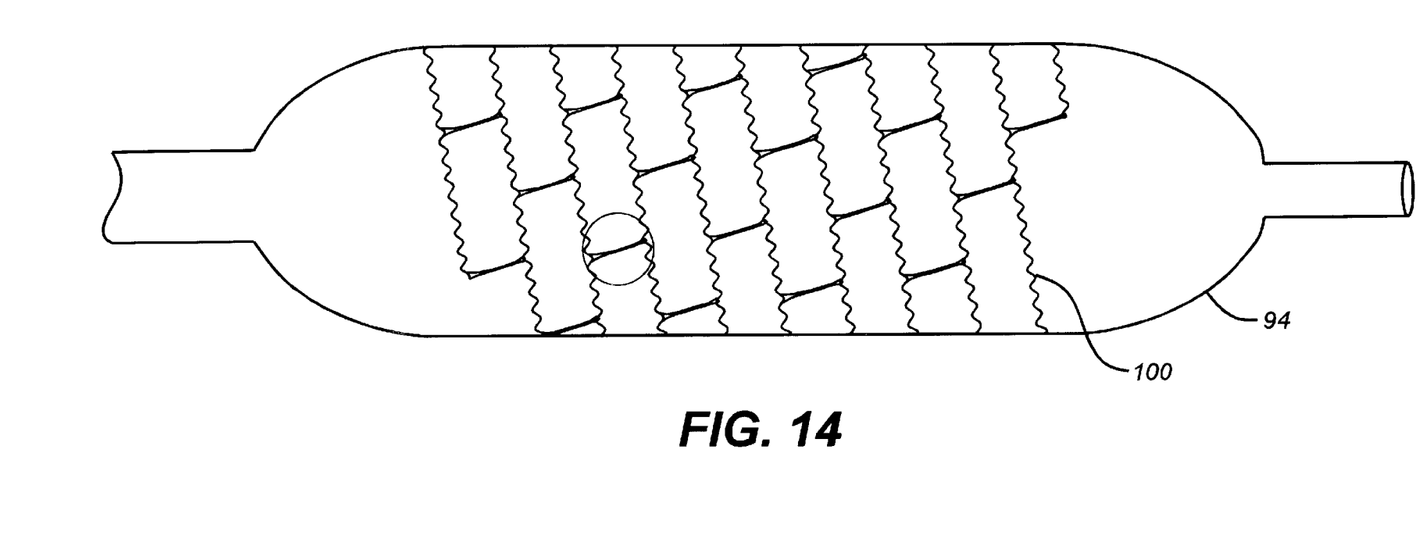
FIG. 14 is an elevational view of a balloon-settable stent using the crossties having the loop feature in combination with the helically wound wire which is, itself, bent into a variety of different shapes, two of which are illustrated in FIGS. 11 and 12.
Figure 14A:
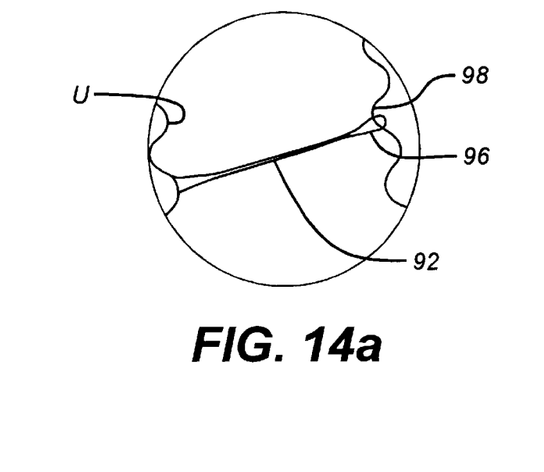

FIGS. 11 and 12 are to be considered in combination with FIG. 14. In this embodiment, the wire may be prebent in a rounded fashion, as shown in FIG. 11, or in an angled fashion, as shown in FIG. 12. These bends are very small, as can be seen in a realistic perspective by looking at FIG. 14. This design can be contrasted with the fairly large bends made in the wire such as 1 in FIG. 1.

In the design of FIG. 14, the undulations of the wire such as, for example, shown in FIGS. 11 and 12, become more readily apparent. In FIG. 14, a typical crosstie 92 is illustrated in the exploded view. The stent in FIG. 14 is expandable with a balloon 94. As the stent grows radially when the balloon 94 is expanded, the crossties 92, which have a loop 96 on at least one end, ride over several or at least one of the undulations represented in FIGS. 11 and 12. The crossties 92 then remain fixated in a position representing the expanded state of the stent between a pair of undulations in a valley, such as 98. As a result, the expanded state of the stent is locked in. The stent may expand as the balloon 94 grows, with loops 96 moving relatively to the undulations of the wires in each row of the helical winding 100. It should be noted that for this embodiment, crossties 92 which have loops 96 can have such loops at one end or both ends without departing from the spirit of the invention.

Figure 18:
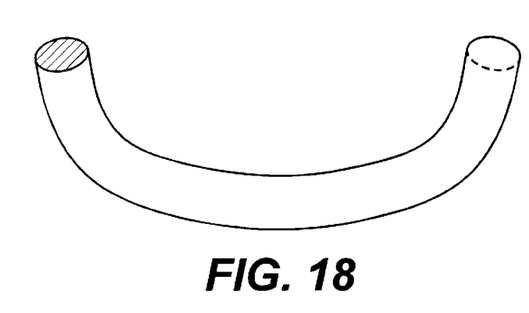
FIG. 18 is a close-up of one of the elements of the stent of the present invention, illustrating one of the preferred embodiments for the cross-section as being round, as compared to the oval section shown in FIG. 1A.

Referring now to FIG. 18, a segment of one of the wires, which has been previously described as shown, indicates the preferred embodiment to be round. The use of a rounded cross-section, such as shown in FIGS. 1A or 18, prevents kinking of the wire segments upon expansion of the stent. Prior designs which have used square or rectangular cross-sections, resulting from using laser cutting techniques and cutting out wire segments from a solid cylinder, have exhibited a tendency of twist such that the wire rings or the helix contain kinks which stick into the flowpath, causing undesirable turbulence. Wire or wire-like material as used herein is intended to encompass a stent made literally of wires or a stent cut from a cylinder down to segments which function similarly to wires.

Figure 20:
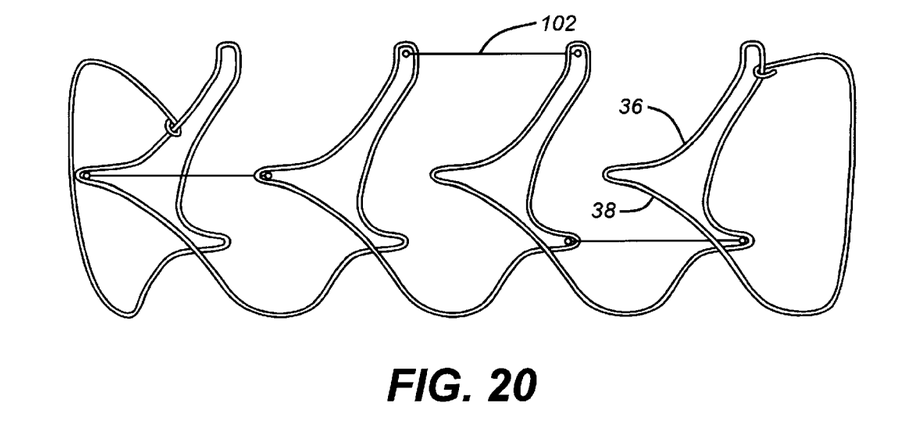
FIG. 20 is the stent of FIG. 19, with the crossties circumferentially offset.

FIGS. 19 and 20 illustrate a helical winding for a stent, employing the sharp angled segments such as 36 and 38, but as contrasted with the design of FIG. 19, the crossties 102 are circumferentially offset in this particular case by 120°, which means that every third crosstie 102 is in longitudinal alignment. Other degrees of offset are within the purview of the invention. While straight crossties have been shown in FIGS. 19 and 20, it is within the purview of the invention to use crossties that have additional flexibility of a bend or more in them to accommodate the needs of bending for the stent.

Figure 15:
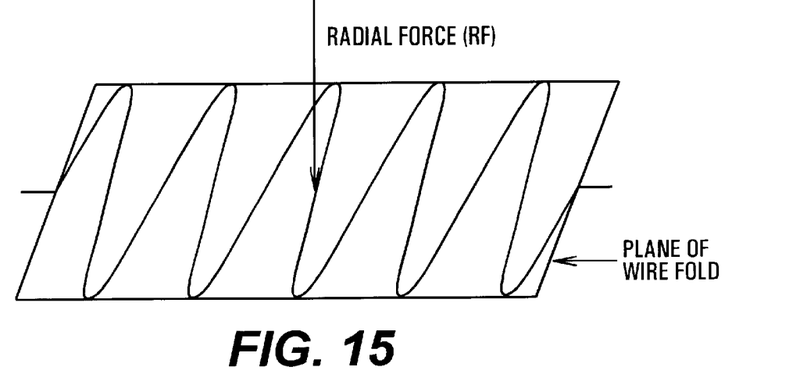
FIG. 15 illustrates a sinusoidally wound wire on a mandrel as known in the prior art.
Figure 16:
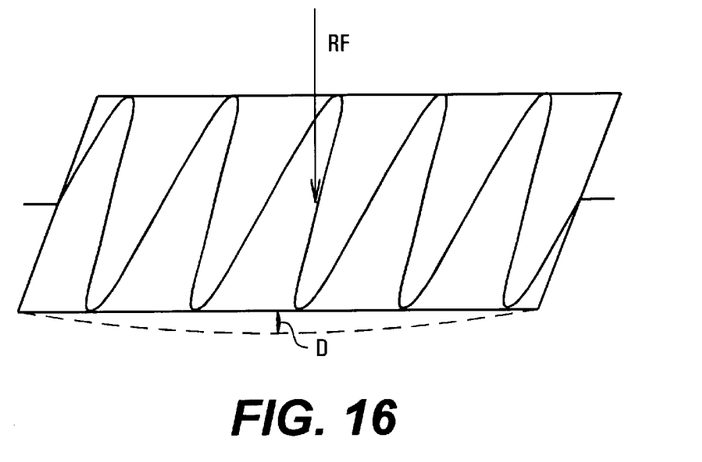
FIG. 16 illustrates the response of such a design to a radial load.
Figure 17:
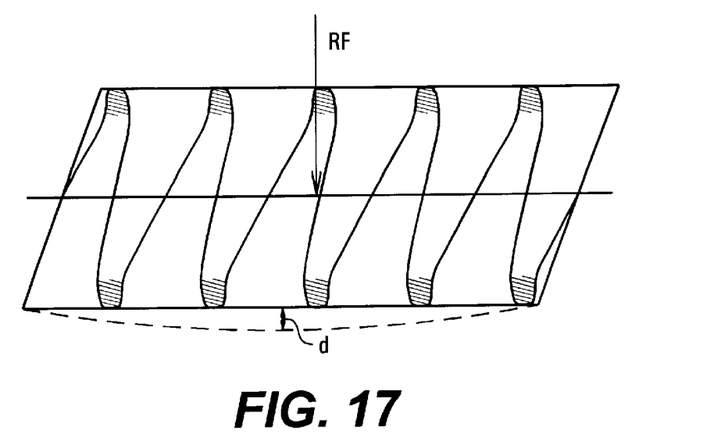
FIG. 17 illustrates one of the embodiments of the invention involving angulated bends and a transverse bend in combination, illustrating its response to a similar load as that placed on the stent shown in FIG. 16.

FIGS. 15–17 illustrate some of the advantages of the use of the second bend, such as bent-up ends 42 and 44 in FIG. 19. FIG. 15 illustrates a simple wound helix in a sinusoidal pattern, subjected to a lateral loading and illustrating in FIG. 16 the measured deflection as D. FIG. 17 illustrates that by using sharply angled corners, in combination with the turning out in a second bend of the angled corner into a plane transversing or intersecting with the plane of the winding, again as illustrated in FIGS. 19 and 13, the net deflection is d, which is significantly less.

This illustration brings to the fore several salient advantages of the various embodiments previously described.

The stents as above described can be made of a metal, such as stainless steel, platinum, nickel titanium, copper-tin alloy, or other suitable biocompatible metals. The stents as illustrated can be cut from a tube whose wall thickness is between about 0.003"–0.10", using known laser techniques, so that the wire crosssection is rounded, such as illustrated in FIGS. 18 or 1A. The stents illustrated can also be made from wire by bending the wire, as illustrated, to form the sharp angles as described. The crossties can be a more rigid, straight design or a more flexible design incorporating one or more bends. In lieu of a multi-ring design, a helix turned on a mandrel, using crossties, such as shown in FIG. 19, can also be employed.

The sharp corners of the various designs indicated provide a uniform rigidity as well as resistance to recoil. The sharp angles, when expanded by the a device such as a balloon 94 or when made from spring steel and simply pre-compressed and allowed to expand in the vascular cavity, resist recoil and tend to keep their expanded shape far better than wire bent in a rounded fashion. By further bending each sharp angle into a different plane with a second bend, an anchoring device is created, plus the sharp angle itself is made far stiffer to again retain the expanded position of the stent against the wall of the vascular flowpath.

The expanded diameter of the stents illustrated above can range from about 2 mm–25 mm. As illustrated in FIG. 5, a polymeric sheath having a mesh appearance can be attached to the outer periphery of the stent. This sheath can be made from polymers such as expanded fluoropolymer, polyethylene, dacron, polyurethane, or similar materials in a thin layer. During expansion, the polymeric layer undergoes plastic deformation. Holes or slits can be made in the plastic sheath in order to facilitate the plastic deformation and stretch of the stent to expand to its final diameter.

In the embodiment such as shown in FIG. 14, the separation between each layer of strands or the pitch is between preferably 2 mm–4 mm. The various stents illustrated in the figures can be delivered by a balloon such as 94 or can be made from spring steel and delivered in a compressed state with a sheath that is removed to allow the stent to spring outwardly radially for fixation. Another way to deliver such a stent is to twist it about its longitudinal axis, which results in a reduction of its outside diameter. Various clip-type devices or sleeves can then be employed to retain it in its reduced diameter state for delivery to the appropriate location in the body. At this time the retraction devices, be they clips or sleeves, can be shifted to allow the stent to take advantage of the potential energy stored in it from twisting so that it can spring out and fixate itself in the appropriate location. The circumferential offset of the crossties such as, for example, 78 and 80 in FIG. 9, can be varied without departing from the spirit of the invention. Typically, measuring from the longitudinal axis of a stent, the separation between crossties 78 and 80 can be in the range of about 100°–180°. The crossties such as 78 and 80 can be made from a radiopaque material to facilitate subsequent diagnostic procedures. Additionally, the entire stent can be made from radiopaque materials such as stainless steel or solid platinum.

The illustrated stent designs also facilitate application of the stent with lower inflation pressures on a balloon. Typical of known designs is the need to apply approximately 18 atmospheres of pressure to the balloon to obtain proper fixation. The illustrated designs of the present invention are believed to be adequately seated at substantially lower inflation pressures for the balloon in the order of approximately 14 atmospheres.

The illustrated designs present the stent whose length remains relatively constant upon radial expansion. This is accomplished by flexibility in the longitudinal members which prevents the longitudinal shrinkage upon radial expansion characteristic of prior designs. It is this longitudinal shrinking upon radial expansion that has caused the segments of prior stent designs to twist into the flowpath of the stent, causing unwanted turbulence. The use of rounded members, such as illustrated in FIGS. 1A and 18, further helps to minimize the twist effect in conjunction with crossties that have some flexibility to them. In the preferred embodiment of FIGS. 2, 2a, 6, and 7, the crossties are preferably made of "wire" having the following characteristics: The wire is normally annealed stainless steel having a diameter of 0.005"–0.010".

In the embodiment illustrated in FIG. 1, the bends 8 define and include an acute angle between 0°–90° with a preferred range of 15°, with the segment lengths of segments 12 and 14 being approximately 0.2 mm long and the crosstie lengths of crossties 3 being approximately 0.2 mm long. In the embodiment shown in FIG. 2A, the apexes 16–18 are again sharp angles formed by the wire, which can be acute or obtuse. Opposed sides 104 and 106 are preferably approximately 2–3 mm long, while the connecting segment 108 between apexes 16 and 18 is preferably approximately 2 mm long. The preferred range of angles for the apexes 16 and 18 is between 90° and 100°. The insertion length of crossties, such as 3 in FIG. 2, which have flexibility to them, is approximately 3 mm. When expanded to their maximum length, they are approximately 2–3 mm long in the preferred embodiment.

Again it should be noted that in the embodiments illustrated in FIGS. 1–10, 13, and 19–20, it is preferred that each wire ring or coil of a helix has a wire structure that has "sharp" bends as opposed to rounded bends. The "sharp" angular bends of the wire give the assembled structure, be it a series of rings or a continuous helix, the rigidity to resist recoil upon expansion. In essence, once such a structure is plastically deformed, it better holds its expanded shape than a wire structure with rounded turns. By further bending the apexes into a different plane, as illustrated, for example, in FIG. 19, the tendency to hold the expanded shape is increased. In the preferred embodiment, the plane of parallel components 42 and 44 with respect to the plane of legs 36 and 38 defines an included offset angle of approximately 30°. This offset is illustrated by angle A as seen in FIG. 13. Typically, the parallel components 42 and 44 with apex 46 protrude outwardly toward the build-up 52 inside the vessel wall 50 by approximately 0.02"–0.04" in the preferred embodiment, as measured from the normal outer periphery of the expanded stent, which, for that much extension of the anchor mechanisms or apexes 46, generally has an expanded outer diameter of 0.120" to 0.200".

Another advantage of some of the designs illustrated, such as the wire ring design of FIG. 10, is that they can easily be cut down to a required size without risk of unraveling. The same can be said for the embodiment such as FIGS. 1 and 2. The use of the crossties provides longitudinal bracing which further assists in promoting structural integrity of the stents, even if cut to a predetermined size. As opposed to using spring steel, the balloon-expandable versions of the stents illustrated above can be made from annealed steel and expanded with a balloon. The embodiments using spring steel or piano wire need to be held in a compressed state with a retractor and when positioned in the appropriate place, the retractor is relaxed and the stent is allowed to snap into place.

It should be noted that while certain configurations of bent wires having sharp angles have been illustrated, such as the general V-shape of FIG. 1 and a general U-shape of FIG. 2A, other geometric shapes can be used as long as the bent wire has sharp angles. The more bends per unit space, the more flexibility to bend around turns in the vascular system the stent will have. However, as the number of bends per unit space is increased, the ability of the stent to resist the radially inward or hoop stresses created by the vascular structure is decreased. Additionally, as more bends are employed, the cost to manufacture the catheter is increased.

It should be noted that with the embodiment of FIG. 14, the ability to withstand the hoop stresses imposed by the vascular structure occurs due to the interlocking of the crosstie 92 in a valley 98 formed by a wire structure that has undulations as shown in FIGS. 11 or 12. Other types of undulations in the wire, along the scale necessary to lock the crosstie 92 in position after expansion with a balloon 94, or other mechanisms or devices that allow initial radial expansion to be locked in, are also within the purview of the invention.

The structure of FIG. 14 does not depend on relatively large bends above a mean baseline. When looking at the design of FIG. 14, the undulations from the average value are fairly small but sufficiently large to allow the crosstie 92 to lodge in a valley 98. The undulations must be sufficiently small to allow the loop 96 to traverse one or more undulations as the stent expands. It is this ability of the loop 96 to traverse one or more undulations that allows the stent to be readily expanded in response to inflation of the balloon 94 and thereafter to hold its expanded position.

The foregoing disclosure and description of the invention are illustrative and explanatory thereof, and various changes in the size, shape and materials, as well as in the details of the illustrated construction, may be made without departing from the spirit of the invention.

I claim:

1. A stent comprising:
    a radially flexible tubular structure made from a plurality of windings comprising peaks and valleys of a wire-like material about a longitudinal axis;
    said wire-like material incorporating sharp first bends formed by at least two of segments of said wire-like material approaching each other for substantially their entire length;
    said segments meeting at a point or becoming parallel to each other immediately before being joined;
    at least one crosstie extending generally longitudinally to connect at least one of said windings to another of said windings; and
    said sharp first bends, expanded beyond the original diameter, to resist recoil of the stent toward its original diameter.

2. A stent comprising:
    a radially flexible tubular structure made from a plurality of windings comprising peaks and valleys of a wire-like material about a longitudinal axis;
    said wire-like material incorporating sharp first bends formed by at least two of segments of said wire-like material approaching each other for substantially their entire length;
    said segments meeting at a point or becoming parallel to each other immediately before being joined;
    at least one crosstie extending generally longitudinally to connect at least one of said windings to another of said windings;
    said at least one crosstie is formed to be flexible to change its length in response to a bending force applied to said tubular structure;
    said sharp first bends, when plastically expanded beyond the original diameter, to resist recoil of the stent toward its original diameter.

3. The stent of claim 1, further comprising:
    at least one second bend formed adjacent said first bends, said first bends disposing said wire-like material in a first plane while said second bend alters at least one of said sharp first bends out of said first plane and into an intersecting plane where an apex is formed.

4. The stent of claim 3, wherein said second bend turns said apex outwardly away from the longitudinal axis of said tubular structure.

5. The stent of claim 4, further comprising a plurality of second bends wherein some of said second bends are in planes not parallel to other second bends.

6. The stent of claim 1, wherein some of said sharp first bends are oppositely oriented with respect to said sharp first bends on other windings.

7. A stent comprising:
    a radially flexible tubular structure made from a plurality of windings comprising peaks and valleys of a wire-like material about a longitudinal axis;
    said wire-like material incorporating sharp first bends formed by at least two of segments of said wire-like material approaching each other for substantially their entire length;
    said segments meeting at a point or becoming parallel to each other immediately before being joined;
    at least one crosstie extending generally longitudinally to connect at least one of said windings to another of said windings;
    said sharp first bends, expanded beyond the original diameter, to resist recoil of the stent toward its original diameter; and
    at least some of said sharp first bends are similarly oriented between adjacent windings but are circumferentially out of phase with other sharp first bends on an adjacent winding.

8. The stent of claim 1, wherein at least some of said sharp first bends are similarly oriented between adjacent windings but are circumferentially in phase with other sharp first bends on an adjacent winding.

9. The stent of claim 7, wherein said at least one crosstie is formed to be flexible to change its length in response to a bending force applied to said tubular structure.

10. The stent of claim 8, wherein said at least one crosstie is formed to be flexible to change its length in response to a bending force applied to said tubular structure.

11. The stent of claim 7, further comprising a plurality of crossties wherein at least one of said crossties between a first winding and a second winding is circumferentially misaligned from said crossties which extend between said second winding and a third winding.

12. The stent of claim 8, further comprising a plurality of crossties wherein at least one of said crossties between a first winding and a second winding is circumferentially misaligned from said crossties which extend between said second winding and a third winding.

13. The stent of claim 3, wherein said second bend is disposed on each of said segments prior to said apex, with said sharp first bend defined by said approaching segments up to said second bend, said segments beyond said second bend coming together to define a rounded configuration of said apex.

14. The stent of claim 13, wherein at least one said second bend turns said apex outwardly away from the longitudinal axis of said tubular structure.

15. The stent of claim 14, wherein each apex is turned away from said longitudinal axis obliquely to said sharp first bend.

16. The stent of claim 15, further comprising a plurality of second bends wherein said second bends are disposed in intersecting planes.

17. The stent of claim 13, wherein said at least one crosstie is flexible to change its length in response to a bending force applied to said tubular structure.

18. The stent of claim 13, wherein at least some of said sharp first bends are similarly oriented between adjacent windings but are circumferentially out of phase with other sharp first bends on an adjacent winding.

19. The stent of claim 13, wherein at least some of said sharp first bends are similarly oriented between adjacent windings but are circumferentially in phase with other sharp first bends on an adjacent winding.

20. The stent of claim 1, wherein said wire-like material has at least a partially rounded cross-section.

21. The stent of claim 20, wherein said wire-like material is formed of a metal which gives the stent a characteristic of a spring when formed into a tubular structure.

22. The stent of claim 20, wherein said wire-like material is formed of an annealed metal which must be mechanically expanded for use of the stent.

23. The stent of claim 1, wherein said tubular structure is formed from discrete rings of said wire-like material, secured to each other by a plurality of crossties.

24. A stent comprising:

a radially flexible tubular structure made from a plurality of windings comprising peaks and valleys of a wire-like material about a longitudinal axis;

said wire-like material incorporating sharp first bends formed by at least two of segments of said wire-like material approaching each other for substantially their entire length;

said segments meeting at a point or becoming parallel to each other immediately before being joined;

at least one crosstie extending generally longitudinally to connect at least one of said windings to another of said windings;

said sharp first bends, expanded beyond the original diameter, to resist recoil of the stent toward its original diameter; and said tubular structure is formed from a continuous spirally wound wire-like material where a plurality of said crossties connect said windings.

25. The stent of claim 2, wherein said tubular structure is formed from discrete rings of said wire-like material, secured to each other by a plurality of crossties.

26. The stent of claim 2, wherein said tubular structure is formed from a continuous spirally wound wire-like material and further comprises a plurality of crossties which connect said windings.

27. The stent of claim 3, wherein said tubular structure is formed from discrete rings of said wire-like material, secured to each other by a plurality of crossties.

28. The stent of claim 3, wherein said tubular structure is formed from a continuous spirally wound wire-like material and further comprises a plurality of crossties which connect said windings.

29. A stent, comprising:

a radially flexible tubular structure made from a plurality of windings about a longitudinal axis of an undulating wire-like material, incorporating a plurality of undulations along its length; and at least one crosstie spanning a pair of said windings and forming a loop over said undulations thereby permitting relative unidirectional movement between said loop and differing undulations on at least one of said windings which are thereby engaged.

30. The stent of claim 29, wherein:

said at least one crosstie is formed having a loop extending around said undulating wire-like material at said end thereof;

said plurality of windings are radially expandable, facilitated by said relative movement as said loop allows movement therethrough of said undulating wire-like element, whereupon attaining the desired radial expansion of said windings, said loop is retained between said undulations to minimize recoil.

31. The stent of claim 30, wherein said undulations are formed with angled bends.

32. The stent of claim 30, wherein said undulations are formed with rounded bends.

* * * * *